(12) United States Patent
Yamanaka et al.

(10) Patent No.: US 8,993,329 B2
(45) Date of Patent: Mar. 31, 2015

(54) METHOD OF EFFICIENTLY ESTABLISHING INDUCED PLURIPOTENT STEM CELLS

(75) Inventors: Shinya Yamanaka, Kyoto (JP); Koji Tanabe, Kyoto (JP)

(73) Assignee: Kyoto University, Kyoto (JP)

( * ) Notice: Subject to any disclaimer, the term of this patent is extended or adjusted under 35 U.S.C. 154(b) by 228 days.

(21) Appl. No.: 13/393,158

(22) PCT Filed: Sep. 22, 2010

(86) PCT No.: PCT/JP2010/067016
§ 371 (c)(1),
(2), (4) Date: Apr. 16, 2012

(87) PCT Pub. No.: WO2011/037270
PCT Pub. Date: Mar. 31, 2011

(65) Prior Publication Data
US 2012/0214243 A1   Aug. 23, 2012

Related U.S. Application Data

(60) Provisional application No. 61/245,478, filed on Sep. 24, 2009.

(51) Int. Cl.
*C12N 15/00* (2006.01)
*C12N 5/00* (2006.01)
*C12N 5/074* (2010.01)

(52) U.S. Cl.
CPC ........ *C12N 5/0696* (2013.01); *C12N 2501/602* (2013.01); *C12N 2501/603* (2013.01); *C12N 2501/604* (2013.01); *C12N 2501/608* (2013.01); *C12N 2510/00* (2013.01)
USPC ......................................... 435/455; 435/235

(58) Field of Classification Search
USPC ................................................ 435/455, 325
See application file for complete search history.

(56) References Cited

U.S. PATENT DOCUMENTS 8,058,065 B2 * 11/2011 Yamanaka et al. ............ 435/377
2009/0227032 A1   9/2009 Yamanaka et al.
2009/0246875 A1  10/2009 Yamanaka et al.

FOREIGN PATENT DOCUMENTS

EP   2 096 169 A1   9/2009
JP   2010-158171 A   7/2010
WO   WO 2008/118820 A2  10/2008
WO   WO 2009/057831 A1   5/2009
WO   WO 2009/096049 A1   8/2009
WO   WO 2011/016588 A1   2/2011

OTHER PUBLICATIONS

Thomson (1995, PNAS, vol. 92, pp. 7844-7848).*
Takahashi (Cell, 2006, vol. 126:663-676).*
Yu (Science, Nov. 20, 2007, vol. 318, p. 1917-1920).*
Blelloch (Cell Stem Cell, Sep. 13, 2007, vol. 1, p. 245-247).*
Nakagawa (Nat Biotechnol, 2008, vol. 26: 101-106).*
Kim (Nature, Jul. 2008, vol. 454, No. 7204, p. 646).*
Aasen (Nature Biotech., Nov. 2008, vol. 26, No. 11, p. 1276-1284).*
Loh (Blood, May 28, 2009, vol. 113, No. 22, p. 5476-5479).*
Feng (Cell Stem Cell, Apr. 3, 2009, vol. 4, p. 301-312).*
Guo (Gene, 2006, vol. 384, p. 51-61).*
Heo (Molecular Cell, 2008, vol. 32, p. 276-284).*
Viswanathan (Nature Genetics, Jul. 2009, vol. 41, No. 7, p. 843-849).*
Cotterman et al., *PloS One*, 4(6): e5799 (2009).
Guo et al., *Gene*, 384: 51-61 (2006).
Lu et al., *Eur. J. Cancer*, 45(12): 2212-2218 (2009).
Tanabe et al., *Abstracts of the 32nd Annual Meeting of the Molecular Biology Society of Japan*, 32nd (vol. 2), p. 191, 2P-0603 (Dec. 2009).
Tanabe et al., *Seigaku*, 1T25-11, 1P-1112 (2008).
Welstead et al., *Current Opinion in Genetics and Development*, 18(2): 123-129 (2008).
Yu et al., *Science*, 318: 1917-1920 (2007).
Japanese Patent Office, International Search Report in International Patent Application No. PCT/JP2010/067016 (Dec. 28, 2010).
Chang et al., *Proceedings of the National Academy of Sciences of the USA*, 106(9): 3384-3389 (Mar. 3, 2009).
Darr et al., *Stem Cells*, 27(2): 352-362 (2009).
Liao et al., *Cell Research*, 18(5): 600-603 (2008).
Viswanathan et al., *Science*, 320(5872): 97-100 (Apr. 4, 2008).
Zhao et al., *Journal of Cellular Biochemistry*, 105(4): 949-955 (2008).
European Patent Office, Extended European Search Report in European Patent Application 10818938.2 (Aug. 26, 2013).

* cited by examiner

*Primary Examiner* — Michael C. Wilson
(74) *Attorney, Agent, or Firm* — Leydig, Voit & Mayer, Ltd.

(57) ABSTRACT

Provided are a method of improving iPS cell establishment efficiency, comprising the step of transferring Lin28B or a nucleic acid that encodes Lin28B to a somatic cell, particularly to a somatic cell on which Lin28 is ineffective or less effective than Lin28B in improving iPS cell establishment efficiency, and a method of producing an iPS cell, comprising the step of transferring Lin28B or a nucleic acid that encodes Lin28B and a nuclear reprogramming substance to a somatic cell. Also provided are an iPS cell comprising a nucleic acid that encodes Lin28B, that can be obtained by the method of producing an iPS cell, and a method of somatic cell production by forcing the iPS cell to differentiate into a somatic cell.

6 Claims, 2 Drawing Sheets

METHOD OF EFFICIENTLY ESTABLISHING INDUCED PLURIPOTENT STEM CELLS

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 13,266 bytes ASCII (Text) file named "709947SequenceListing.txt," created Feb. 28, 2012.

TECHNICAL FIELD

The present invention relates to a method of improving the efficiency of establishing induced pluripotent stem cells (hereinafter referred to as iPS cells) and a reagent therefor, more specifically to a method of improving the efficiency of establishing iPS cells, comprising the step of transferring Lin28B or a nucleic acid that encodes Lin28B to somatic cells, to a reagent for improving the efficiency of establishing iPS cells, containing Lin28B or a nucleic acid that encodes Lin28B, and the like.

BACKGROUND OF THE INVENTION

In recent years, mouse and human iPS cells have been established one after another. Yamanaka et al. induced iPS cells by transferring the Oct3/4, Sox2, Klf4 and c-Myc genes into mouse fibroblasts to force the cells to express the genes [WO 2007/069666 A1; Takahashi, K. and Yamanaka, S., *Cell*, 126: 663-676 (2006)]. Later, it was revealed that iPS cells could also be established with 3 factors excluding the c-Myc gene [Nakagawa, M. et al., *Nat. Biotechnol.*, 26: 101-106 (2008)]. Furthermore, Yamanaka et al. succeeded in establishing iPS cells by transferring the same 4 genes into human dermal fibroblasts [WO 2007/069666 A1; Takahashi, K. et al., *Cell*, 131: 861-872 (2007)]. On the other hand, Thomson and his group established human iPS cells using Nanog and Lin28 in place of Klf4 and c-Myc [WO 2008/118820 A2; Yu, J. et al., *Science*, 318: 1917-1920 (2007)]. Specifically, it has been shown that the number of colonies of iPS cells (establishment efficiency) is increased by adding Lin28 to the three factors consisting of Oct3/4, Sox2 and Nanog [WO 2008/118820 A2; Yu, J. et al., *Science*, 318: 1917-1920 (2007)]; Lin28 is described as a factor that is not indispensible for reprogramming but acts to improve reprogramming efficiency [WO 2008/118820 A2].

Known as a member of the Lin28 family is Lin28B. Lin28B was originally cloned as a gene overexpressed in hepatocellular carcinoma [Guo Y. et al., *Gene*, 384: 51-61 (2006)]. Lin28B, like Lin28, is an RNA-binding protein, and is known to inhibit the maturation of the microRNA let-7 to influence the differentiation and proliferation of ES cells [Lu L. et al., *Eur. J. Cancer*, 45(12): 2212-2218 (2009)]. Lin28B has also been suggested to mediate the progression of ovarian cancer [Lu L. et al., *Eur. J. Cancer*, 45(12): 2212-2218 (2009)]. However, there has been no disclosure or suggestion regarding the involvement of Lin28B in iPS cell induction.

SUMMARY OF THE INVENTION

It is an object of the present invention to provide a novel method of improving iPS cell establishment efficiency and an establishment efficiency improver.

The present inventors attempted to establish iPS cells by transferring 4 genes consisting of reprogramming factors (Oct3/4, Sox2, Klf4) and Lin28 or Lin28B, a member of the same family, to a somatic cell, and demonstrated that Lin28B is effective in improving iPS cell establishment efficiency (increasing the number of colonies), the effect being equivalent to, or higher than, that of Lin28. The present inventors also found for the first time that there are some somatic cells on which Lin28 is ineffective or very little effective in improving iPS cell establishment efficiency. More surprisingly, the present inventors demonstrated that Lin28B is effective even on such cells on which Lin28 is ineffective (or little effective), and have developed the present invention.

Accordingly, the present invention provides:

[1] A method of improving iPS cell establishment efficiency, comprising the step of transferring Lin28B or a nucleic acid that encodes Lin28B to a somatic cell.

[2] The method according to [1] above, wherein the somatic cell is a somatic cell on which Lin28 is ineffective or less effective than Lin28B in improving iPS cell establishment efficiency.

[3] An iPS cell establishment efficiency improver comprising Lin28B or a nucleic acid that encodes Lin28B.

[4] The agent according to [3] above, wherein the improver is to be transferred to a somatic cell on which Lin28 is ineffective or less effective than Lin28B in improving iPS cell establishment efficiency.

[5] A method of producing an iPS cell, comprising the step of transferring Lin28B or a nucleic acid that encodes Lin28B and a nuclear reprogramming substance to a somatic cell.

[6] The method according to [5] above, wherein the nuclear reprogramming substance is a substance other than Lin28 and a nucleic acid that encodes Lin28.

[7] The method according to [5] above, wherein the nuclear reprogramming substance is selected from the group consisting of members of the Oct family, members of the Sox family, members of the Klf family, members of the Myc family, and Nanog, as well as nucleic acids that encode the same.

[8] The method according to [5] above, wherein the nuclear reprogramming substance comprises Oct3/4, Sox2 and Klf4, or nucleic acids that encode them.

[9] The method according to any one of [5] to [8] above, wherein the somatic cell is a somatic cell on which Lin28 is ineffective or less effective than Lin28B in improving iPS cell establishment efficiency.

[10] An iPS cell inducer from a somatic cell, comprising Lin28B or a nucleic acid that encodes Lin28B and a nuclear reprogramming substance.

[11] The agent according to [10] above, wherein the nuclear reprogramming substance is a substance other than Lin28 and a nucleic acid that encodes Lin28.

[12] The agent according to [10] above, wherein the nuclear reprogramming substance is selected from the group consisting of members of the Oct family, members of the Sox family, members of the Klf family, members of the Myc family, and Nanog, as well as nucleic acids that encode the same.

[13] The agent according to [10] above, wherein the nuclear reprogramming substance comprises Oct3/4, Sox2 and Klf4, or nucleic acids that encode them.

[14] The agent according to any one of [10] to [13] above, wherein the somatic cell is a somatic cell on which Lin28 is ineffective or less effective than Lin28B in improving iPS cell establishment efficiency.

[15] An iPS cell containing an exogenous nucleic acid that encodes Lin28B.

[16] The iPS cell according to [15] above, wherein the exogenous nucleic acid that encodes Lin28B is integrated in the genome.
[17] A method of producing a somatic cell, comprising performing a differentiation induction treatment on the iPS cell according to [15] or [16] above to cause the iPS cell to differentiate into a somatic cell.
[18] A method of producing a somatic cell, comprising the steps of:
(1) producing an iPS cell by the method according to any one of [5] to [9] above, and
(2) performing a differentiation induction treatment on the iPS cell obtained through the step (1) to cause the iPS cell to differentiate into a somatic cell.
[19] A use of Lin28B or a nucleic acid that encodes Lin28B for improving iPS cell establishment efficiency.
[20] The use according to [19] above, wherein the use is for transfer to a somatic cell on which Lin28 is ineffective or less effective than Lin28B in improving iPS cell establishment efficiency.
[21] A use of Lin28B or a nucleic acid that encodes Lin28B for producing an iPS cell, wherein Lin28B or the nucleic acid is transferred to a somatic cell along with a nuclear reprogramming substance.
[22] The use according to [21] above, wherein the nuclear reprogramming substance is a substance other than Lin28 or a nucleic acid that encodes Lin28.
[23] The use according to [21] above, wherein the nuclear reprogramming substance is selected from the group consisting of members of the Oct family, members of the Sox family, members of the Klf family, members of the Myc family, and Nanog, as well as nucleic acids that encode the same.
[24] The use according to [21] above, wherein the nuclear reprogramming substance comprises Oct3/4, Sox2 and Klf4, or nucleic acids that encode them.
[25] The use according to any one of [21] to [24] above, wherein the somatic cell is a somatic cell on which Lin28 is ineffective or less effective than Lin28B in improving iPS cell establishment efficiency.
[26] A use of the iPS cell according to [15] or [16] above in producing a somatic cell.
[27] The iPS cell according to [15] or [16] above as a source of cells for producing a somatic cell.

Because Lin28B is effective even on somatic cells on which Lin28 is ineffective or very little effective in improving iPS cell establishment efficiency, as stated above, it can be widely used to induce iPS cells without limitations on the choice of somatic cell.

DETAILED DESCRIPTION OF THE INVENTION

Figure 1:
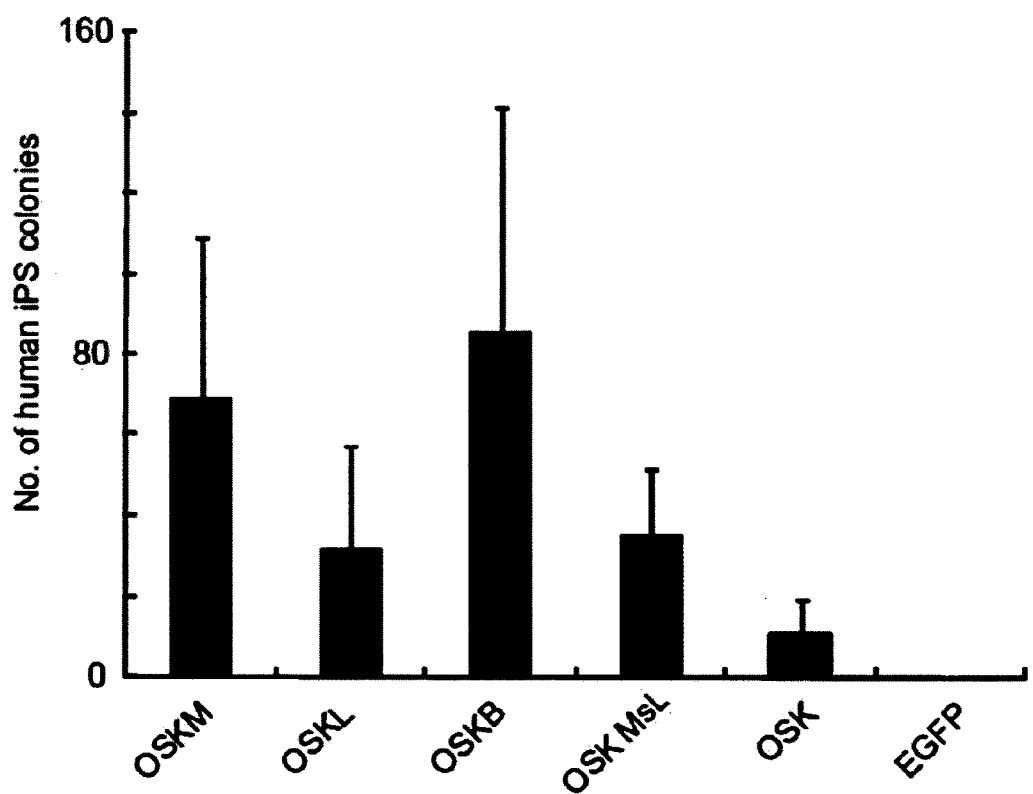
FIG. 1 is a graph showing the results of Example 1, wherein the axis of ordinates indicates the number of iPS cell colonies, and "O" stands for human Oct3/4, "S" for human Sox2, "K" for human Klf4, "M" for human c-Myc, "L" for human Lin28, "B" for human Lin28B, and "MsL" for mouse Lin28.

The present invention provides a method of improving iPS cell establishment efficiency by transferring Lin28B or a nucleic acid that encodes Lin28B to a somatic cell in the step of nuclear reprogramming of the somatic cell. While nuclear reprogramming of a somatic cell is achieved by transferring a nuclear reprogramming substance to the somatic cell, the present invention also provides a method of producing an iPS cell by transferring Lin28B or a nucleic acid that encodes Lin28B and a nuclear reprogramming substance to a somatic cell. Herein, cases where iPS cells cannot be established by merely transferring a nuclear reprogramming substance alone to a somatic cell, but can be established by transferring a nuclear reprogramming substance along with Lin28B or a nucleic acid that encodes Lin28B, are also deemed as corresponding to "an improvement of establishment efficiency."

(a) Sources of Somatic Cells

In the present invention, any cells other than germ cells of mammalian origin (e.g., humans, mice, monkeys, bovines, pigs, rats, dogs etc.) can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells (tissue progenitor cells) thereof and the like. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as nerve stem cells, hematopoietic stem cells, mesenchymal stem cells, and dental pulp stem cells.

The choice of mammal individual as a source of somatic cells is not particularly limited; however, when the iPS cells obtained are to be used for regenerative medicine in humans, it is particularly preferable, from the viewpoint of prevention of graft rejection, to collect the somatic cells from a patient or another person with the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA type wherein major HLAs (e.g., the three gene loci of HLA-A, HLA-B and HLA-DR) are identical (hereinafter the same meaning shall apply) and the like. When the iPS cells obtained are not to be administered (transplanted) to a human, but used as, for example, a source of cells for screening for evaluating a patient's drug susceptibility or adverse reactions, it is likewise desired to collect the somatic cells from the patient or another person with the same genetic polymorphism correlating with the drug susceptibility or adverse reactions.

When the somatic cell used is a somatic cell on which Lin28 is ineffective or less effective than Lin28B in improving iPS cell establishment efficiency, the method of the present invention, wherein Lin28B or a nucleic acid that encodes Lin28B is transferred to the somatic cell, is particularly useful.

Somatic cells isolated from a mammal can be pre-cultured is using a medium known per se suitable for their cultivation according to the choice of cells before being subjected to the step of nuclear reprogramming. Examples of such media include, but are not limited to, minimal essential medium (MEM), Dulbecco's modified Eagle medium (DMEM), RPMI1640 medium, 199 medium, F12 medium, and the like supplemented with about 5 to 20% fetal calf serum. When a transfer reagent such as cationic liposome, for example, is used in bringing the somatic cell into contact with Lin28B or a nucleic acid that encodes Lin28B, and nuclear reprogramming substances (and another iPS cell establishment efficiency improver described below if required), it is sometimes preferable that the medium has been replaced with a serum-free medium so as to prevent the transfer efficiency from decreasing.

(b) Lin28B or a Nucleic Acid that Encodes Lin28B

Lin28B as used in the present invention is a protein comprising the same or substantially the same amino acid sequence as the amino acid sequence shown by SEQ ID NO:2. The Lin28B protein may be isolated and purified from a cell or tissue [e.g., cells and tissues of thymus, bone marrow, spleen, brain, spinal cord, heart, skeletal muscle, kidney, lung, liver, pancreas or prostate, progenitor cells, stem cells or cancer cells of these cells, and the like] of a human or another mammal (e.g., mouse, rat, monkey, pig, dog and the like) by a protein separation and purification technique known per se, or may be a recombinant protein produced by a gene recombination technique known per se using a nucleic acid that encodes Lin28B, or a protein produced by cell-free protein synthesis.

"A protein comprising substantially the same amino acid sequence as the amino acid sequence shown by SEQ ID NO:2" is a protein that comprises an amino acid sequence having an identity of about 80% or more, more preferably about 90% or more, still more preferably about 95% or more, to the amino acid sequence of human Lin28B shown by SEQ ID NO:2, and that possesses an activity equivalent to the activity of the amino acid sequence shown by SEQ ID NO:2. Here, "activity" refers to an effect in improving iPS cell establishment efficiency, and "substantially the same quality" means that the effect is equivalent to, or higher than, the effect of Lin28 on an optionally chosen somatic cell. The effect in improving iPS cell establishment efficiency can be evaluated by comparing the number of emerging iPS cell colonies between a case where only specified reprogramming factors (e.g., 3 factors consisting of Oct3/4, Sox2 and Klf4) are transferred to a somatic cell and a case where in addition to the reprogramming factors, Lin28B (or Lin28) is transferred.

Examples of Lin28B as used in the present invention also include proteins comprising (i) an amino acid sequence having one or two or more amino acids [e.g., 1 to about 10, preferably 1 to several (5, 4, 3, or 2) amino acids] deleted from the amino acid sequence shown by SEQ ID NO:2, (ii) an amino acid sequence having one or two or more amino acids [e.g., 1 to about 10, preferably 1 to several (5, 4, 3, or 2) amino acids] added to the amino acid sequence shown by SEQ ID NO:2, (iii) an amino acid sequence having one or two or more amino acids [e.g., 1 to about 10, preferably 1 to several (5, 4, 3, or 2) amino acids] inserted into the amino acid sequence shown by SEQ ID NO:2, (iv) an amino acid sequence having one or two or more amino acids [e.g., 1 to about 10, preferably 1 to several (5, 4, 3, or 2) amino acids] substituted by other amino acids in the amino acid sequence shown by SEQ ID NO:2, or (v) an amino acid sequence comprising a combination thereof, and possessing an activity equivalent to that of the amino acid sequence shown by SEQ ID NO:2. When an amino acid sequence is inserted, deleted or substituted as described above, the position of the insertion, deletion or substitution is not subject to limitations, as far as the iPS cell establishment efficiency improving effect is retained.

Examples of preferred Lin28B proteins include human Lin28B consisting of the amino acid sequence shown by SEQ ID NO:2 (RefSeq Accession No. NP_001004317.1), and orthologs thereof in other mammals (e.g., mouse ortholog registered with GenBank under RefSeq Accession No. NP_001026942.1, rat ortholog registered under RefSeq Accession No. XP_001069344.1 and the like), as well as naturally occurring allelic mutants and polymorphisms thereof and the like. It is desirable that the Lin28B used be of the same animal species from which the transfer subject somatic cell is derived.

Transfer of Lin28B protein to a somatic cell can be achieved using a method known per se for protein transfer into a cell. Such methods include, for example, the method using a protein transfer reagent, the method using a protein transfer domain (PTD)—or cell penetrating peptide (CPP)—fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. Lin28B is diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as drosophila-derived AntP, HIV-derived TAT (Frankel, A. et al, *Cell* 55, 1189-93 (1988) or Green, M. & Loewenstein, P. M. Cell 55, 1179-88 (1988)), Penetratin (Derossi, D. et al, *J. Biol. Chem.* 269, 10444-50 (1994)), Buforin II (Park, C. B. et al. *Proc. Natl. Acad. Sci. USA* 97, 8245-50 (2000)), Transportan (Pooga, M. et al. *FASEB J.* 12, 67-77 (1998)), MAP (model amphipathic peptide) (Oehlke, J. et al. *Biochim. Biophys. Acta.* 1414, 127-39 (1998)), K-FGF (Lin, Y. Z. et al. *J. Biol. Chem.* 270, 14255-14258 (1995)), Ku70 (Sawada, M. et al. *Nature Cell Biol.* 5, 352-7 (2003)), Prion (Lundberg, P. et al. *Biochem. Biophys. Res. Commun.* 299, 85-90 (2002)), pVEC (Elmquist, A. et al. *Exp. Cell Res.* 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G. L. *Cancer Res.* 60, 6551-6 (2000)), and HSV-derived VP22. CPPB derived from PTDs include polyarginines such as 11R (*Cell Stem Cell*, 4, 381-384 (2009)) and 9R (*Cell Stem Cell*, 4, 472-476 (2009)).

A fused protein expression vector incorporating cDNA of a Lin28B and PTD sequence or CPP sequence is prepared, and recombination expression is performed using the vector. The fused protein is recovered and used for transfer. Transfer can be performed in the same manner as above except that a protein transfer reagent is not added.

Microinjection, a method of placing a protein solution in a glass needle having a tip diameter of about 1 μm, and injecting the solution into a cell, ensures the transfer of the protein into the cell.

Other useful methods of protein transfer include the electroporation method, the semi-intact cell method [Kano, F. et al. Methods in Molecular Biology, Vol. 322, 357-365 (2006)], and transfer using the Wr-t peptide [Kondo, E. et al., Mol. Cancer. Ther. 3(12), 1623-1630 (2004)] and the like.

The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

The nucleic acid that encodes Lin28B used in the present invention may be any nucleic acid that encodes the Lin28B protein in any one of the above-described aspects of the present invention. The nucleic acid may be a DNA or an RNA, or a DNA/RNA chimera, with preference given to a DNA. The nucleic acid may be double-stranded or single-stranded. In the case of double strands, the nucleic acid may be a double-stranded DNA, a double-stranded RNA or a DNA:RNA hybrid.

A DNA that encodes Lin28B can be cloned from a cDNA derived from a cell or tissue [e.g., cells and tissues of thymus, bone marrow, spleen, brain, spinal cord, heart, skeletal muscle, kidney, lung, liver, pancreas or prostate, progenitor cells, stem cells or cancer cells of these cells, and the like] of a human or another mammal (e.g., mice, rats, monkeys, pigs, dogs and the like) by a conventional method.

Examples of nucleic acids that encode Lin28B include a nucleic acid comprising the base sequence shown by SEQ ID NO:1, or a nucleic acid which contains a base sequence capable of hybridizing with a sequence complementary to the base sequence shown by SEQ ID NO:1 under stringent conditions, and which encodes a protein possessing an activity substantially equivalent to the activity of the aforementioned Lin28B. A useful nucleic acid capable of hybridizing with a sequence complementary to the base sequence shown by SEQ ID NO:1 under stringent conditions is a nucleic acid comprising a base sequence having an identity of about 80% or more, preferably about 90% or more, more preferably about 95% or more, to the base sequence shown by SEQ ID NO:1. Examples of stringent conditions include conditions described in Current Protocols in Molecular Biology, John Wiley & Sons, 6.3.1-6.3.6, 1999, e.g., hybridization with 6×SSC (sodium chloride/sodium citrate)/45° C. followed by not less than one time of washing with 0.2×SSC/0.1% SDS/50 to 65° C.; those skilled art can choose as appropriate hybridization conditions that give equivalent stringency.

The nucleic acid that encodes Lin28B is preferably a nucleic acid comprising the base sequence that encodes human Lin28B, shown by SEQ ID NO:1 (RefSeq Accession No. NM_001004317.2), an ortholog thereof in another mammal (e.g., mouse ortholog registered with GenBank under RefSeq Accession No. NM_001031772.1, rat ortholog registered under RefSeq Accession No. XM_001069344.1 and the like), or a naturally occurring allelic mutant or polymorphisms thereof. It is desirable to use a nucleic acid that encodes Lin28B of the same animal species as the animal from which the transfer subject somatic cell is derived.

Transfer of a nucleic acid that encodes Lin28B to a somatic cell can be achieved using a method of gene transfer to cells known per se. A nucleic acid that encodes Lin28B is inserted into an appropriate expression vector comprising a promoter capable of functioning in a host somatic cell. Useful expression vectors include, for example, viral vectors such as retrovirus, lentivirus, adenovirus, adeno-associated virus, herpesvirus and Sendai virus, plasmids for the expression in animal cells (e.g., pA1-11, pXT1, pRc/CMV, pRc/RSV, pcDNAI/Neo) and the like.

The type of a vector to be used can be chosen as appropriate according to the intended use of the iPS cell to be obtained. Useful vectors include adenovirus vector, plasmid vector, adeno-associated virus vector, retrovirus vector, lentivirus vector, Sendai virus vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

A nucleic acid that encodes Lin28B may be integrated alone into an expression vector, or along with one or more reprogramming genes into an expression vector. Preference is given to the former case when using a retrovirus or lentivirus vector, which offer high gene transfer efficiency, and to the latter case when using a plasmid, adenovirus, or episomal vector and the like, but there are no particular limitations.

In the context above, when a nucleic acid that encodes Lin28B and one or more reprogramming genes are integrated in one expression vector, these genes can preferably be integrated into the expression vector via a sequence enabling polycistronic expression. By using a sequence enabling polycistronic expression, it is possible to more efficiently express a plurality of genes integrated in one expression vector. Useful sequences enabling polycistronic expression include, for example, the 2A sequence of foot-and-mouth disease virus (SEQ ID No:6; PLoS ONE 3, e2532, 2008, Stem Cells 25, 1707, 2007), the IRES sequence (U.S. Pat. No. 4,937,190) and the like, with preference given to the 2A m sequence.

An expression vector harboring a nucleic acid that encodes Lin28B can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to a cell by a method suitable for the viral vector. For example, specific means using a retroviral vector are disclosed in WO2007/69666, *Cell*, 126, 663-676 (2006) and *Cell*, 131, 861-872 (2007). Specific means using a lentivirus vector is disclosed in *Science*, 318, 1917-1920 (2007). When iPS cells are utilized as a source of cells for regenerative medicine, the expression (reactivation) of Lin28B or the activation of a gene present in the vicinity of the site where the Lin28B gene is integrated potentially increases the risk of carcinogenesis in tissues regenerated from differentiated cells of iPS cell derivation; therefore, a nucleic acid that encodes Lin28B is preferably expressed transiently, without being integrated into the chromosome of the cells. From this viewpoint, it is preferable to use an adenoviral vector, which is unlikely to be integrated into the chromosome, is preferred. Specific means using an adenoviral vector is described in Science, 322, 945-949 (2008). Adeno-associated virus is unlikely to be integrated into the chromosome, and is less cytotoxic and less phlogogenic than adenoviral vectors, so that it is another preferred vector. Sendai virus vectors are capable of being stably present outside of the chromosome, and can be degraded and removed using an siRNA as required, so that they are preferably utilized as well. Useful Sendai virus vectors are described in *J. Biol. Chem.*, 282, 27383-27391 (2007) or JP-B-3602058.

When a retroviral vector or a lentiviral vector is used, even if silencing of the transgene has occurred, it possibly becomes reactivated; therefore, for example, a method can be used preferably wherein a nucleic acid that encodes Lin28B is cut out using the Cre-loxP system, when becoming unnecessary. That is, with loxP sequences arranged on both ends of the nucleic acid in advance, iPS cells are induced, thereafter the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivated (SIN) LTR prepared by deleting the sequence, or substituting the sequence with a polyadenylation sequence such as of SV40. Specific means using the Cre-loxP system and SIN LTR is disclosed in Soldner et al., *Cell*, 136: 964-977 (2009), Chang et al., *Stem Cells*, 27: 1042-1049 (2009), etc.

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, *Science*, 322, 949-953 (2008) and the like.

When a plasmid vector, an adenovirus vector and the like are used, the gene transfer can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfer can be performed once or more optionally chosen times (e.g., once to 10 times, once to 5 times or the like), preferably the transfer can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature*, 458: 771-775 (2009), Woltjen et al., *Nature*, 458: 766-770 (2009).

Another preferable non-integration type vector is an episomal vector, which is capable of autonomous replication outside of the chromosome. Specific means using an episomal vector is disclosed by Yu et al., in *Science*, 324, 797-801 (2009). Where necessary, an expression vector may be constructed by inserting a nucleic acid that encodes Lin28B into an episomal vector having loxP sequences placed in the same orientation on the 5' and 3' sides of a vector component essential for the replication of the episomal vector, and transferred to a somatic cell.

Examples of the episomal vector include a vector comprising as a vector component a sequence derived from EBV, SV40 and the like necessary for autonomous replication. The vector component necessary for autonomous replication is specifically exemplified by a replication origin and a gene that encodes a protein that binds to the replication origin to control the replication; examples include the replication origin oriP and the EBNA-1 gene for EBV, and the replication origin on and the SV40 large T antigen gene for SV40.

The episomal expression vector comprises a promoter that controls the transcription of a nucleic acid that encodes Lin28B. The promoter used may be as described above. The episomal expression vector may further contain as desired an enhancer, a polyadenylation signal, a selection marker gene and the like, as described above. Examples of the selection marker gene include the dihydrofolate reductase gene, the neomycin resistance gene and the like.

The loxP sequences useful in the present invention include, in addition to the bacteriophage P1-derived wild type loxP sequence (SEQ ID NO:3), optionally chosen mutant loxP sequences capable of deleting the sequence flanked by the loxP sequence by recombination when placed in the same orientation at positions flanking a vector component necessary for the replication of the transgene. Examples of such mutant loxP sequences include lox71 (SEQ ID NO:4), mutated in 5' repeat, lox66 (SEQ ID NO:5), mutated in 3' repeat, and lox2272 and lox511, mutated in spacer portion. Although the two loxP sequences placed on the 5' and 3' sides of the vector component may be identical or not, the two mutant loxP sequences mutated in spacer portion must be identical (e.g., a pair of lox2272 sequences, a pair of lox511 sequences). Preference is given to a combination of a mutant loxP sequence mutated in 5' repeat (e.g., lox71) and a mutant loxP sequence mutated in 3' repeat (e.g., lox66). In this case, the loxP sequences remaining on the chromosome have double mutations in the repeats on the 5' side and 3' side as a result of recombination, and are therefore unlikely to be recognized by Cre recombinase, thus reducing the risk of causing a deletion mutation in the chromosome due to unwanted recombination. When the mutant loxP sequences lox71 and lox66 are used in combination, each may be placed on any of the 5' and 3' sides of the aforementioned vector component, but it is necessary that the mutant loxP sequences be inserted in an orientation such that the mutated sites would be located at the outer ends of the respective loxP sequences.

Each of the two loxP sequences is placed in the same is orientation on the 5' and 3' sides of a vector component essential for the replication of the transgene (i.e., a replication origin, or a gene sequence that encodes a protein that binds to the replication origin to control the replication). The vector component flanked by the loxP sequences may be either a replication origin or a gene sequence that encodes a protein that binds to the replication origin to control the replication, or both.

An episomal vector can be transferred into a cell using, for example, the lipofection method, liposome method, electroporation method, calcium phosphate co-precipitation method, DEAE dextran method, microinjection method, gene gun method and the like. Specifically, for example, methods described in *Science*, 324: 797-801 (2009) and elsewhere can be used.

Whether or not the vector component necessary for the replication of the transgene has been removed from the iPS cell can be confirmed by performing a Southern blot analysis or PCR analysis using a nucleic acid comprising a base sequence in the vector component and/or in the vicinity of the loxP sequence as a probe or primer, with the episome fraction isolated from the iPS cell as a template, and determining the presence or absence of a band or the length of the band detected. The episome fraction can be prepared by a method obvious in the art; for example, methods described in *Science*, 324: 797-801 (2009) and elsewhere can be used.

(c) Nuclear Reprogramming Substances

In the present invention, "a nuclear reprogramming substance" may be configured with any substance, such as a proteinous factor or a nucleic acid that encodes the same (including forms incorporated in a vector), or a low molecular compound, as far as it is a substance (substances) capable of inducing an iPS cell from a somatic cell when transferred alone to the somatic cell, or when transferred along with Lin28B or a nucleic acid that encodes Lin28B to the somatic cell. When the nuclear reprogramming substance is a proteinous factor or a nucleic acid that encodes the same, preferable nuclear reprogramming substances are exemplified by the following combinations (hereinafter, only the names for proteinous factors are shown).

(1) Oct3/4, Klf4, c-Myc
(2) Oct3/4, Klf4, c-Myc, Sox2 (here, Sox2 is replaceable with Sox1, Sox3, Sox15, Sox17 or Sox18; Klf4 is replaceable with Klf1, Klf2 or Klf5; c-Myc is replaceable with T58A (active mutant), N-Myc or L-Myc)
(3) Oct3/4, Klf4, c-Myc, Sox2, Fbx15, Nanog, Eras, ECAT15-2, Tcl1, β-catenin (active mutant S33Y)
(4) Oct3/4, Klf4, c-Myc, Sox2, TERT, SV40 Large T antigen (hereinafter, SV40LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmi1
[For details of these combinations, see WO 2007/069666 (however, in the combination (2) above, for replacement of Sox2 with Sox18, and replacement of Klf4 with Klf1 or Klf5, see *Nature Biotechnology*, 26, 101-106 (2008)); for details of the combination "Oct3/4, Klf4, c-Myc, Sox2", see also *Cell*, 126, 663-676 (2006), *Cell*, 131, 861-872 (2007) and the like; for details of the combination "Oct3/4, Klf2 (or Klf5), c-Myc, Sox2", see also *Nat. Cell Biol.*, 11, 197-203 (2009); for details of the combination "Oct3/4, Klf4, c-Myc, Sox2, hTERT, SV40LT", see also *Nature*, 451, 141-146 (2008)]
(9) Oct3/4, Klf4, Sox2 [see *Nature Biotechnology*, 26, 101-106 (2008)]
(10) Oct3/4, Sox2, Nanog, Lin28 [see *Science*, 318, 1917-1920 (2007)]
(11) Oct3/4, Sox2, Nanog, Lin28, hTERT, SV40LT [see *Stem Cells*, 26, 1998-2005 (2008)]
(12) Oct3/4, Klf4, c-Myc, Sox2, Nanog, Lin28 [see *Cell Research* (2008) 600-603]
(13) Oct3/4, Klf4, c-Myc, Sox2, SV40LT [see *Stem Cells*, 26, 1998-2005 (2008)]
(14) Oct3/4, Klf4 [see *Nature*, 454:646-650 (2008), Cell Stem Cell, 2:525-528 (2008)]
(15) Oct3/4, c-Myc [see *Nature*, 454:646-650 (2008)]
(16) Oct3/4, Sox2 [see Nature, 451, 141-146 (2008), WO2008/118820]
(17) Oct3/4, Sox2, Nanog (see WO2008/118820)
(18) Oct3/4, Sox2, Lin28 (see WO2008/118820)
(19) Oct3/4, Sox2, c-Myc, Esrrb [here, Esrrb is replaceable with Esrrg; see *Nat. Cell Biol.*, 11, 197-203 (2009)]
(20) Oct3/4, Sox2, Esrrb [see *Nat. Cell Biol.*, 11, 197-203 (2009)]
(21) Oct3/4, Klf4, L-Myc
(22) Oct3/4, Nanog
(23) Oct3/4 [*Cell*, 136: 411-419 (2009), *Nature*, 08436, doi: 10.1038 published online (2009)]
(24) Oct3/4, Klf4, c-Myc, Sox2, Nanog, Lin28, SV40LT [see *Science*, 324: 797-801 (2009)]

In (1)-(24) above, in place of Oct3/4, other members of the Oct family, for example, Oct1A, Oct6 and the like, can also be used. In place of Sox2 (or Sox1, Sox3, Sox15, Sox17, Sox18), other members of the Sox family, for example, Sox7 and the like, can also be used. Furthermore, when Lin28 is included as a nuclear reprogramming substance in (1)-(24) above, it is preferable that other factors than Lin28 be used in combination.

A combination which does not fall in any one of (1) to (24) above, but which comprises all the constituents of any one thereof and an optionally chosen other substance, can also be included in the scope of "nuclear reprogramming substances" in the present invention. Provided that the somatic cell to undergo nuclear reprogramming is endogenously expressing one or more of the constituents of any one of (1) to (24) above at a level sufficient to cause nuclear reprogramming, a combination of only the remaining constituents excluding the endogenously expressed constituents can also be included in the scope of "nuclear reprogramming substances" in the present invention.

Of these combinations, one comprising at least one, preferably 2 or more, more preferably 3 or more, different substances selected from among Oct3/4, Sox2, Klf4, c-Myc, Nanog and SV40LT is preferred.

Particularly, if a use of the iPS cells obtained for therapeutic purposes is born in mind, the combination of the three factors Oct3/4, Sox2 and Klf4 [combination (9) above] is preferably used. If a use of the iPS cells obtained for therapeutic purposes is not born in mind (e.g., used as an investigational tool for drug discovery screening and the like), the combination of the three factors, as well as four factors consisting of the three factors and c-Myc, five factors consisting of the four factors and Nanog, and six factors consisting of the five factors and SV40 Large T, and the like are exemplified.

Furthermore, combinations of the same factors as those shown above, but c-Myc is replaced with L-Myc, are also preferred nuclear reprogramming substances.

Information on the mouse and human cDNA sequences of the aforementioned proteinous factors is available with reference to the NCBI accession numbers mentioned in WO 2007/069666 (in the publication, Nanog is described as ECAT4; mouse and human cDNA sequence information on Lin28, Esrrb, Esrrg, and L-Myc can be acquired by referring to the following NCBI accession numbers, respectively); those skilled in the art are able to easily isolate these cDNAs.

| Gene name | Mouse | Human |
| --- | --- | --- |
| Lin28 | NM_145833 | NM_024674 |
| Esrrb | NM_011934 | NM_004452 |
| Esrrg | NM_011935 | NM_001438 |
| L-Myc | NM_008506 | NM_001033081 |

When a proteinous factor is used as a nuclear reprogramming substance, it can be prepared by inserting the cDNA obtained into an appropriate expression vector, transferring it into a host cell, culturing the cell, and recovering the recombinant proteinous factor from the culture. Meanwhile, when a nucleic acid that encodes a proteinous factor is used as a nuclear reprogramming substance, the cDNA obtained is inserted into a viral vector, episomal vector or plasmid vector in the same manner as with the above-described case of a nucleic acid that encodes Lin28B to construct an expression vector, which is subjected to the nuclear reprogramming step. The aforementioned Cre-loxP system or piggyBac transposon system can also be utilized as required. When two or more nucleic acids that encodes a proteinous factor are transferred to a cell as nuclear reprogramming substances, the different nucleic acids may be carried by separate vectors, or the plurality of nucleic acids may be joined in tandem to obtain a polycistronic vector. In the latter case, to allow efficient polycistronic expression, it is desirable that the 2A self-cleaving peptide of foot-and-mouth disease virus be inserted between the nucleic acids [see Science, 322, 949-953 (2008) and the like].

Contact of a nuclear reprogramming substance with a somatic cell can be achieved (a) in the same manner as with the above-described Lin28B protein when the substance is a proteinous factor, or (b) in the same manner as with the above-described nucleic acid that encodes Lin28B when the substance is a nucleic acid that encodes the proteinous factor (a). Meanwhile, (c) when the nuclear reprogramming substance is a low molecular compound, this contact can be achieved by dissolving the substance in an aqueous or non-aqueous solvent at an appropriate concentration, adding the resulting solution of the substance to a medium suitable for cultivation of somatic cells isolated from a human or another mammal (e.g., minimal essential medium (MEM), Dulbecco's modified Eagle medium (DMEM), RPMI1640 medium, 199 medium, F12 medium and the like supplemented with about 5 to 20% fetal bovine serum) to obtain a nuclear reprogramming substance concentration in a range where the substance is sufficiently effective in nuclear reprogramming without causing cytotoxicity, and culturing the cells for a given length of period. The nuclear reprogramming substance concentration varies depending on the kind of nuclear reprogramming substance used, and is chosen as appropriate over the range of about 0.1 nM to about 100 nM.

Duration of contact is not particularly limited, as far as it is sufficient to achieve nuclear reprogramming of the cells; usually, the nuclear reprogramming substance may be allowed to be co-present in the medium until a positive colony emerges.

(d) iPS Cell Establishment Efficiency Improvers

Since the iPS cell establishment efficiency has been low, various substances that improve the efficiency have recently been proposed one after another. It can be expected, therefore, that the iPS cell establishment efficiency will be increased by bringing another establishment efficiency improver, in addition to Lin28B or a nucleic acid that encodes Lin28B and a nuclear reprogramming substances as described above, into contact with the transfer subject somatic cell.

Examples of iPS cell establishment efficiency improvers include, but are not limited to, histone deacetylase (HDAC) inhibitors [e.g., low-molecular inhibitors such as valproic acid (VPA) (Nat. Biotechnol., 26 (7): 795-797 (2008)), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], DNA methyltransferase inhibitors (e.g., 5'-azacytidine) (Nat. Biotechnol., 26(7): 795-797 (2008)), G9a histone methyltransferase inhibitors [e.g., low-molecular inhibitors such as BIX-01294 (Cell Stem Cell, 2: 525-528 (2008)), nucleic acid-based expression inhibitors such as siRNAs and shRNAs against G9a (e.g., G9a siRNA (human) (Santa Cruz Biotechnology) and the like) and the like], L-channel calcium agonists (e.g., Bayk8644) (Cell Stem Cell, 3, 568-574 (2008)), p53 inhibitors (e.g., siRNA and shRNA against p53 (Cell Stem Cell, 3, 475-479 (2008)), UTF1 (Cell Stem Cell, 3, 475-479 (2008)), Wnt Signaling (e.g., soluble Wnt3a) (Cell Stem Cell, 3, 132-135 (2008)), 21/LIF (21 is an inhibitor of mitogen-activated protein kinase signalling and glycogen synthase kinase-3, PloS Biology, 6 (10), 2237-2247 (2008)), and ES cell-specific miRNAs [e.g., miR-302-367 cluster (Mol. Cell. Biol. doi: 10.1128/MCB.00398-08), miR-302 (RNA (2008) 14: 1-10), miR-291-3p, miR-294 and miR-295 (Nat. Biotechnol. 27: 459-461 (2009))]. As mentioned above, the nucleic acid-based expression inhibitors may be in the form of expression vectors harboring a DNA that encodes an siRNA or shRNA.

Of the aforementioned constituents of nuclear reprogramming substances, SV40 large T antigen, for example, can also be included in the scope of iPS cell establishment efficiency improvers because it is an auxiliary factor unessential for the nuclear reprogramming of somatic cells. While the mechanism of nuclear reprogramming remains unclear, it does not matter whether auxiliary factors, other than the factors essential for nuclear reprogramming, are deemed nuclear reprogramming substances or iPS cell establishment efficiency improvers. Hence, because the somatic cell nuclear reprogramming process is taken as an overall event resulting from contact of a nuclear reprogramming substance and an iPS cell establishment efficiency improver with a somatic cell, it does not always seems to be essential for those skilled in the art to distinguish between the two.

Contact of an iPS cell establishment efficiency improver with a somatic cell can be achieved as described above with respect to nuclear reprogramming substances, depending on the case where the improver is (a) a proteinous factor, (b) a nucleic acid that encodes the proteinous factor, or (c) a low-molecular compound.

An iPS cell establishment efficiency improver, including Lin28B or a nucleic acid that encodes Lin28B, may be contacted with a somatic cell simultaneously with a nuclear reprogramming substance, and either one may be contacted in advance, as far as the efficiency of iPS cell establishment from a somatic cell improves significantly compared with the efficiency obtained in the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, for example, when the nuclear reprogramming substance and iPS cell establishment efficiency improver are both used in the form of a viral vector or plasmid vector, both may be simultaneously transferred into the cell.

(e) Improving the Establishment Efficiency by Culture Conditions iPS cell establishment efficiency can further be improved by culturing the cells under hypoxic conditions in the nuclear reprogramming process for somatic cells. As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.95% or more and the like), or 1% or more (e.g., 1.1% or more, 1.2% or more, 1.3% or more, 1.4% or more and the like).

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be started before the somatic cell is contacted with Lin28B or a nucleic acid that encodes Lin28B and the nuclear reprogramming substance, or at the same time as the contact, or after the contact, it is preferable, for example, that the culture under hypoxic conditions be started just after the somatic cell is contacted with Lin28B or a nucleic acid that encodes Lin28B and the nuclear reprogramming substance, or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency at normal oxygen concentrations and the like.

After being contacted with Lin28B or a nucleic acid that encodes Lin28B and a nuclear reprogramming substance (and an iPS cell establishment efficiency improver), the cell can, for example, be cultured under conditions suitable for cultivation of ES cells. In the case of mouse cells, the cultivation is carried out with the addition of leukemia inhibitory factor (LIF) as a differentiation suppression factor to an ordinary medium. Meanwhile, in the case of human cells, it is desirable that basic fibroblast growth factor (bFGF) and/or stem cell factor (SCF) be added in place of LIF. Usually, the cell is cultured in the co-presence of mouse embryonic fibroblasts (MEFs) treated with radiation or an antibiotic to terminate the cell division, as feeder cells. Usually, STO cells and the like are commonly used as MEFs; for induction of an iPS cell, however, the SNL cell [McMahon, A. P. & Bradley, A. Cell 62, 1073-1085 (1990)] and the like are commonly used. Co-culture with the feeder cells may be started before contact with Lin28B or a nucleic acid that encodes Lin28B and a nuclear reprogramming substance, at the time of the contact, or after the contact (for example, 1-10 days later).

A candidate colony of iPS cells can be selected in two ways: methods with drug resistance and reporter activity as indicators, and methods based on macroscopic examination of morphology. As an example of the former, a colony positive for drug resistance and/or reporter activity is selected using a recombinant cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant cells include MEFs derived from a mouse having the βgeo (which encodes a fusion protein of β-galactosidase and neomycin phosphotransferase) gene knocked in to the Fbx15 gene locus [Takahashi & Yamanaka, *Cell*, 126, 663-676 (2006)], and MEFs derived from a transgenic mouse having the green fluorescent protein (GFP) gene and the puromycin resistance gene integrated in the Nanog gene locus [Okita et al., *Nature*, 448, 313-317 (2007)]. Meanwhile, methods for selecting a candidate colony by macroscopic examination of morphology include, for example, the method described by Takahashi et al. in *Cell*, 131, 861-872 (2007). Although the methods using reporter cells are convenient and efficient, colony selection by macroscopic examination is desirable from the viewpoint of safety when iPS cells are prepared for therapeutic purposes in humans.

The identity of the cells of the selected colony as iPS cells can be confirmed by positive responses to Nanog (or Oct3/4) reporters (puromycin resistance, GFP positivity and the like), as well as by the visible formation of an ES cell-like colony, as described above; however, to ensure greater accuracy, it is possible to perform tests such as alkaline phosphatase staining, analyzing the expression of various ES-cell-specific genes, and transplanting the selected cells to a mouse and confirming teratoma formation.

When a nucleic acid that encodes Lin28B is transferred to a somatic cell, the iPS cell obtained is a novel cell distinct from conventionally known iPS cells in that the exogenous nucleic acid is contained. In particular, when the exogenous nucleic acid is introduced into a somatic cell using a retrovirus, lentivirus or the like, the exogenous nucleic acid is usually integrated in the genome of the iPS cell obtained, so that the phenotype of containing the exogenous nucleic acid is stably retained.

The iPS cells thus established can be used for various purposes. For example, by utilizing a method of differentiation induction reported with respect to ES cells, differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person of the same or substantially the same HLA type would enable stem cell therapy by autogeneic transplantation, wherein the iPS cells are differentiated into desired cells (that is, cells of an affected organ of the patient, cells that have a therapeutic effect on disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the invention is never limited.

EXAMPLES

Example 1

Comparison of Effects of Lin28 and Lin28B on Establishment of iPS Cells (1)

Adult human dermal fibroblasts (HDF)(a 36-year-old female Caucasian, cell name 1388) were allowed to express the mouse ecotropic virus receptor Slc7a1 gene using a lentivirus (pLenti6/UbC-Slc7a1), as described by Takahashi, K. et al. in Cell, 131:861-872 (2007). These cells ($1 \times 10^5$ cells/well, E-well plate) were transfected with the following genes using a retrovirus, as described by Takahashi, K. et al. in Cell, 131:861-872 (2007).
1) Human Oct3/4, Sox2, Klf4, c-Myc
2) Human Oct3/4, Sox2, Klf4, Lin28
3) Human Oct3/4, Sox2, Klf4, Lin28B
4) Human Oct3/4, Sox2, Klf4, and mouse Lin28
5) Human Oct3/4, Sox2, Klf4

For control, the EGFP gene alone was transferred.

Seven days after the viral infection, the cells were recovered and re-seeded onto feeder cells ($5 \times 10^5$ cells/100 mm dish). The feeder cells used were SNL cells treated with mitomycin C to terminate the cell division thereof [McMahon, A. P. & Bradley, A. Cell 62, 1073-1085 (1990)]. Starting 10 days after the infection, the cells were cultured in a primate ES cell culture medium (ReproCELL) supplemented with 4 ng/ml recombinant human bFGF (WAKO). 40 days after the infection, iPS cell colonies were counted; the results are shown in FIG. 1. When Lin28 or Lin28B was added to 3 factors (Oct3/4, Sox2, Klf4), the number of iPS colonies increased. This effect in increasing the number of colonies was higher with Lin28B than with Lin28, exceeding the effect of c-Myc.

Example 2

Comparison of Effects of Lin28 and Lin28B on Establishment of iPS Cells (2)

The effects of Lin28 and Lin28B on the establishment of iPS cells were compared using the various human dermal fibroblasts (HDFs) shown in Table 1.

TABLE 1

| Cell name | Race | Sex | Age |
| --- | --- | --- | --- |
| 1503 | Caucasian | Female | 73 years |
| 1616 | Japanese | Female | 68 years |
| TIG 113 | Japanese | Female | 21 years |
| TIG 120 | Japanese | Female | 6 years |
| TIG 121 | Japanese | Male | 8 months |

These HDFs were allowed to express the mouse ecotropic virus receptor Slc7a1 gene using lentivirus (pLenti6/UbC-Slc7a1) according to the method described by Takahashi, K. et al. in Cell, 131:861-872 (2007). Transferred to these cells ($1 \times 10^5$ cells/well, 6-well plate) were the following genes by means of retrovirus according to the method described by Takahashi, K. et al. in Cell, 131:861-872 (2007).
1) Human Oct3/4, Sox2, Klf4, Lin28B
2) Human Oct3/4, Sox2, Klf4, Lin28
3) Human Oct3/4, Sox2, Klf4

For control, the DsRed gene alone was transferred.

Figure 2:
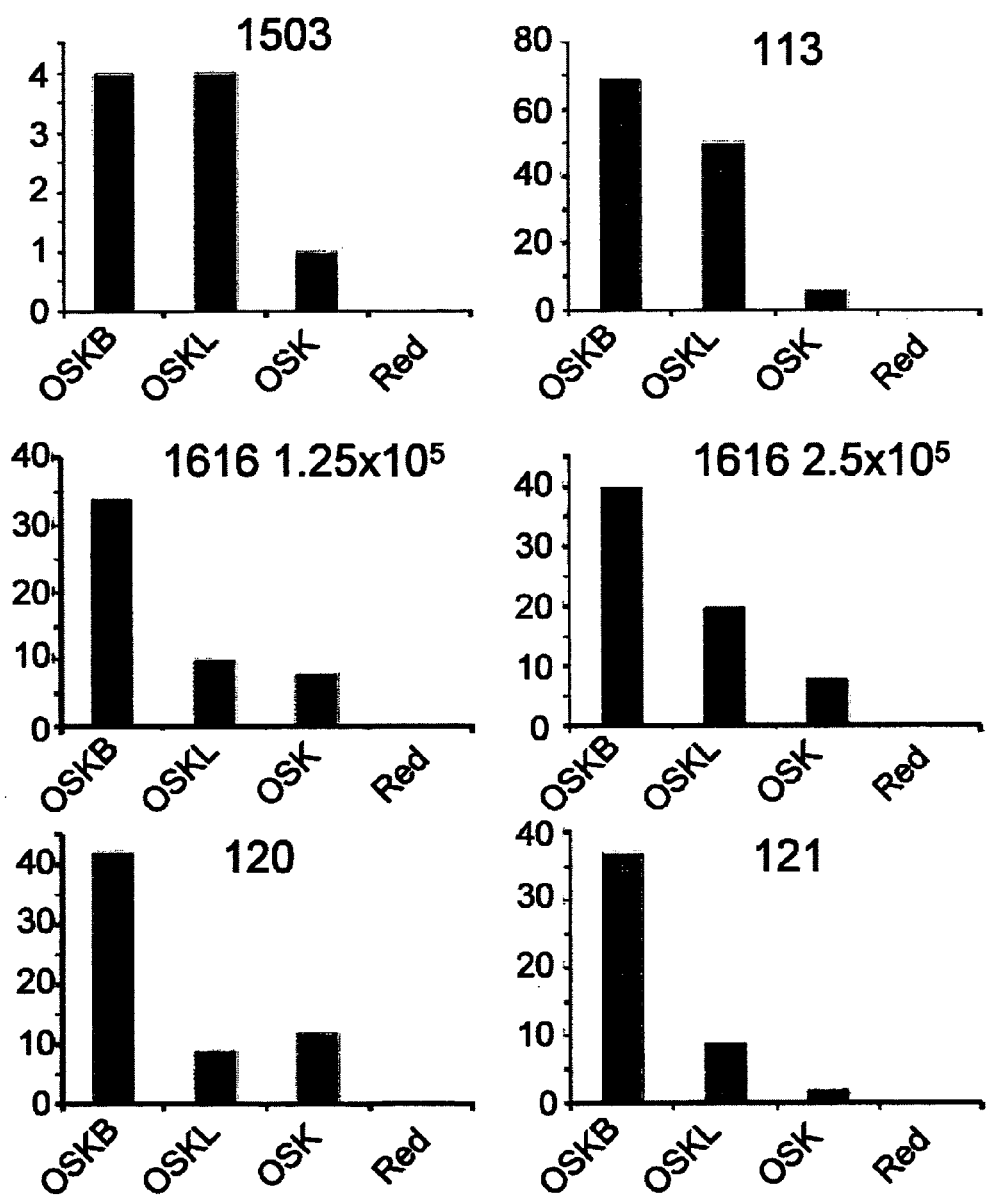
FIG. 2 is a graph showing the results of Example wherein the axis of ordinates indicates the number of iPS cell colonies, and O, S, K, B, and L stand for the same as in FIG. 1.

Seven days after viral infection, the cells were recovered and re-seeded onto feeder cells ($1.25 \times 10^5$ cells/100 mm dish or $2.5 \times 10^5$ cells/100 mm dish). The feeder cells used were SNL cells treated with mitomycin C to terminate the cell division thereof [McMahon, A. P. & Bradley, A. Cell 62, 1073-1085 (1990)]. Starting 10 days after the infection, the cells were cultured in a primate ES cell culture medium (ReproCELL) supplemented with 4 ng/ml recombinant human bFGF (WAKO). 32% days after the infection, iPS cell colonies were counted; the results are shown in FIG. 2. In the lines 1503 and TIG 113, Lin28 and Lin28B were equivalently effective in increasing the number of iPS cell colonies. Meanwhile, in the lines 1616, TIG 120, and TIG 121, even when Lin28 was added to the three factors (Oct3/4, Sox2, Klf4), almost no effect was observed, whereas Lin28B proved to be effective on all cell lines in increasing the number of iPS cell colonies. Hence, the effect of Lin28B in increasing the number of iPS cell colonies is equivalent to, or higher than, that of Lin28; Lin28B was shown to be effective even on cells for which Lin28 is ineffective (or little effective).

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "Claims."

In addition, the contents described in any publication cited herein, including patents and patent applications, are hereby incorporated in their entireties by reference, to the extent that they have been disclosed herein.

This application is based on U.S. provisional patent application No. 61/245,478, the contents of which are hereby incorporated by reference.

The invention claimed is:

1. A method of improving induced pluripotent stem (iPS) cell establishment efficiency, comprising transferring Lin28B or a nucleic acid that encodes Lin28B to a somatic cell undergoing nuclear reprogramming, wherein the nuclear reprogramming is brought about by contacting the somatic cells with nuclear reprogramming substances comprising (a) Oct3/4 or a nucleic acid that encodes Oct3/4, (b) Sox2 or a nucleic acid that encodes Sox2, and (c) Klf4 or a nucleic acid that encodes Klf4, thereby improving iPS cell establishment efficiency.

2. The method according to claim 1, wherein the somatic cell is a somatic cell on which Lin28 is ineffective or less effective than Lin28B in improving iPS cell establishment efficiency.

3. A method of producing an iPS cell, comprising the step of transferring Lin28B or a nucleic acid that encodes Lin28B and nuclear reprogramming substances to a somatic cell, wherein the nuclear reprogramming substances comprise (a) Oct3/4 or a nucleic acid that encodes Oct3/4, (b) Sox2 or a nucleic acid that encodes Sox2, and (c) Klf4 or a nucleic acid that encodes Klf4, thereby producing an iPS cell.

4. The method according to claim 3, wherein the nuclear reprogramming substances do not comprise Lin28 and a nucleic acid that encodes Lin28.

5. The method according to claim 3, wherein the nuclear reprogramming substances are (a) Oct3/4 or a nucleic acid that encodes Oct3/4, (b) Sox2 or a nucleic acid that encodes Sox2, and (c) Klf4 or a nucleic acid that encodes Klf4.

6. The method according to claim 3, wherein the somatic cell is a somatic cell on which Lin28 is ineffective or less effective than Lin28B in improving iPS cell establishment efficiency.

* * * * *

SEQUENCE LISTING

<160> NUMBER OF SEQ ID NOS: 6

<210> SEQ ID NO 1
<211> LENGTH: 5504
<212> TYPE: DNA
<213> ORGANISM: Homo sapiens
<220> FEATURE:
<221> NAME/KEY: CDS
<222> LOCATION: (204)..(956)

<400> SEQUENCE: 1

```
aattgacaaa gtcacgtgtg ctcaggggc cagaaactgg agagaggaga gaaaaaaatc      60
aaaagaagga aagcacatta gaccatgcga gctaaatttg tgatcgcaca aaatcaagat    120
gttagattga tgcagaagat cactccgttc caaagggaaa gttttcatct cacgagtttg    180
gagctgaggg cccgtggggc aac atg gcc gaa ggc ggg gct agc aaa ggt ggt    233
                          Met Ala Glu Gly Gly Ala Ser Lys Gly Gly
                            1               5                  10 gga gaa gag ccc ggg aag ctg ccg gag ccg gca gag gag gaa tcc cag      281
Gly Glu Glu Pro Gly Lys Leu Pro Glu Pro Ala Glu Glu Glu Ser Gln
              15                  20                  25 gtt ttg cgc gga act ggc cac tgt aag tgg ttc aat gtg cgc atg gga      329
Val Leu Arg Gly Thr Gly His Cys Lys Trp Phe Asn Val Arg Met Gly
          30                  35                  40 ttt gga ttc atc tcc atg ata aac cga gag gga agc ccc ttg gat att      377
Phe Gly Phe Ile Ser Met Ile Asn Arg Glu Gly Ser Pro Leu Asp Ile
      45                  50                  55 cca gtc gat gta ttt gta cac caa agc aaa cta ttc atg gaa gga ttt      425
Pro Val Asp Val Phe Val His Gln Ser Lys Leu Phe Met Glu Gly Phe
  60                  65                  70 aga agc cta aaa gaa gga gaa cca gtg gaa ttc aca ttt aaa aaa tct      473
Arg Ser Leu Lys Glu Gly Glu Pro Val Glu Phe Thr Phe Lys Lys Ser
 75                  80                  85                  90 tcc aaa ggc ctt gag tca ata cgg gta aca gga cct ggt ggg agc ccc      521
Ser Lys Gly Leu Glu Ser Ile Arg Val Thr Gly Pro Gly Gly Ser Pro
                  95                 100                 105 tgt tta gga agt gaa aga aga ccc aaa ggg aag aca cta cag aaa aga      569
Cys Leu Gly Ser Glu Arg Arg Pro Lys Gly Lys Thr Leu Gln Lys Arg
             110                 115                 120 aaa cca aag gga gat aga tgc tac aac tgt ggt ggc ctt gat cat cat      617
Lys Pro Lys Gly Asp Arg Cys Tyr Asn Cys Gly Gly Leu Asp His His
         125                 130                 135 gct aag gaa tgt agt cta cct cct cag cca aag aag tgc cat tac tgt      665
Ala Lys Glu Cys Ser Leu Pro Pro Gln Pro Lys Lys Cys His Tyr Cys
     140                 145                 150 cag agc atc atg cac atg gtg gca aac tgc cca cat aaa aat gtt gca      713
Gln Ser Ile Met His Met Val Ala Asn Cys Pro His Lys Asn Val Ala
155                 160                 165                 170 cag cca ccc gcg agt tct cag gga aga cag gaa gca gaa tcc cag cca      761
Gln Pro Pro Ala Ser Ser Gln Gly Arg Gln Glu Ala Glu Ser Gln Pro
                 175                 180                 185 tgc act tca act ctc cct cga gaa gtg gga ggc ggg cat ggc tgt aca      809
Cys Thr Ser Thr Leu Pro Arg Glu Val Gly Gly Gly His Gly Cys Thr
             190                 195                 200 tca cca ccg ttt cct cag gag gct agg gca gag atc tca gaa cgg tca      857
Ser Pro Pro Phe Pro Gln Glu Ala Arg Ala Glu Ile Ser Glu Arg Ser
         205                 210                 215 ggc agg tca cct caa gaa gct tcc tcc acg aag tca tct ata gca cca      905
Gly Arg Ser Pro Gln Glu Ala Ser Ser Thr Lys Ser Ser Ile Ala Pro
     220                 225                 230
```

| | | | | | | | | | | | | | | | | |
|---|---|---|---|---|---|---|---|---|---|---|---|---|---|---|---|---|
| gaa | gag | caa | agc | aaa | aag | ggg | cct | tca | gtt | caa | aaa | agg | aaa | aag | aca | 953 |
| Glu | Glu | Gln | Ser | Lys | Lys | Gly | Pro | Ser | Val | Gln | Lys | Arg | Lys | Lys | Thr | |
| 235 | | | | 240 | | | | | 245 | | | | | 250 | | |

| | | | | |
|---|---|---|---|---|
| taa caggtcttct | tcatatgttc | tttcctttac | ccggttgcaa | agtctacctc | 1006 |
| atgcaagtat | aggggaacag | tatttcacaa | gcagtagctg | acctgggatt ttaactacta | 1066 |
| ttggggaact | gtgaattttt | taaacagaca | aatcactcta | agcaaattac atttgagcag | 1126 |
| ggtgtcatgt | tttatgttaa | ttcagagaat | aagatactat | gtctgtcaat atgtgcatgt | 1186 |
| gtgagaggga | gagagcctga | gtctgtgtgt | gtacatgagg | atttttatat aggaatgtag | 1246 |
| acacatatat | aaagaggctt | tgtctttata | tatttgtgta | tagatcaaag cacacaccct | 1306 |
| ctctcatata | attggatatt | tccaagaatt | gaaaacccat | gtgaagcatt atagatagtt | 1366 |
| ttaaatttaa | cccactggag | ttttcttgaa | ataccacttc | ttttatatta tataaaacta | 1426 |
| aaaacacgac | tgttaccttt | tgtgtgaacc | aaaggatact | tcagatctca gagctgccaa | 1486 |
| ttatgggta | ctaaaggttt | ttaagacatc | cagttctccc | gaatttggga ttgcctcttt | 1546 |
| ttcttgaaat | ctctggagta | gtaattttt | tccccctttt | ttgaaggcag taccttaact | 1606 |
| tcatatgcct | ctgactgcca | taagcttttt | tgattctggg | ataacataac tccagaaaag | 1666 |
| acaatgaatg | tgtaatttgg | gccgatattt | cactgtttta | aattctgtgt ttaattgtaa | 1726 |
| aattagatgc | ctattaagag | aaatgaaggg | gaggatcatc | ttagtggctt gttttcagta | 1786 |
| gtattttaat | atcagcttct | tgtaaccttt | tccatgttgt | gagggttgta agggattgtg | 1846 |
| tggcaacagc | agcttcccctt | ggctaactca | atcttctacc | cattgcttag agcagggagc | 1906 |
| cctccttatt | tactactgaa | gaccttagag | aactccaatt | gtttggcata tatttttggt | 1966 |
| ggtggttttt | attcctcctg | gagagttatc | taatttgttt | ctaaaacaaa caagcagcaa | 2026 |
| agaaatgaat | taaatactgg | ggttgagaat | taaaattaag | tggatgttca cagttgccca | 2086 |
| atatatatga | cctgcaaatg | atacgaaaaa | gtgcagcatt | tagtggcagt taacaagagt | 2146 |
| gacaagcctg | gggcagaggt | accaaacctc | tcccaccaga | gagctagaag tattttatac | 2206 |
| agtaactttg | atcttatgga | agtgaccttc | aatgcttatt | ctgaagtaac ctatatggtg | 2266 |
| gatacaggat | gaacattcag | tgccagggag | aatcttctca | ggttggttct cgttagagtg | 2326 |
| ataaactggc | taggggccat | agtattggtc | ctgttaggtt | tcggtcatgg aaaaaaaaat | 2386 |
| tattttgggg | tcatcctggc | tctagatgtt | atgggcaaat | ttctgaaaca tctgcaagaa | 2446 |
| ggtaccagtt | aattatagtg | cttaatattg | ggaataagat | taagcattat aattataatg | 2506 |
| tatgggcctg | ttggtgtaag | ctcagataat | taaataaaaa | tagcatgact caaatgagac | 2566 |
| atattctgct | gaacagtttc | tacttcctct | cccgcctgtc | ctgtcatggg agacgtgtat | 2626 |
| agttgctgct | gtttcagcaa | accaccataa | gacgaaaatg | cctcaggttg ggttgccagt | 2686 |
| cctttacaac | tcagcttgaa | tttcacaaca | gtgattgtga | aatctgcgt ggtatacact | 2746 |
| gaaatatcgg | tgtgctgtga | tgcaaagctt | acctttgacg | atattgaatg tgatatagct | 2806 |
| gtagagaagt | acttccttgc | cttatgtgag | gatttcaaac | ttatttaaat tatgtagaca | 2866 |
| aatcaaagtg | gcattgctta | atttttagca | ggcataataa | gcaagttaac agtaaaatgc | 2926 |
| aaaacatgat | aagcgttgct | caatttttag | caggtataat | aagcaggtta acagtaaaaa | 2986 |
| tgcaaaacat | gatagataag | tcactttgaa | aattcaaacc | aaagttcctt caccttatgg | 3046 |
| aaataggaaa | ttatggactt | caaaattgga | cacttcctgt | ttacaaaaag aaattcagag | 3106 |
| ctaaaatcat | ggtaaaaaaa | aatagaaaca | cttgagaact | atggtcttta tgggtgcaat | 3166 |
| ttgaaatcct | tttcatcatc | ttaccagact | aaactaagag | cacataccaa acctatctta | 3226 |

```
tggttgaaag ttggggttta tttttatat gagaatatta tcactattac ataacatact    3286
caggacaaag aactttgctc agggaacata ccatgtaata tttttgttgt ttctttacag    3346
actagtctac agtcctgctt actcaaaaca aaccaaataa cttataccct tatataagta    3406
ttatgtactg atgatagtaa ctacctctga gtttgacaca gatcaaaatt tttgaatatc    3466
agatatcagt tatcctattt ttatttcatg tgaaaactcc tctaaagcag attccctcaa    3526
ctctgtgcat atgtgaatat cactgatgtg aacacattgt tcatttacat aggtaaaata    3586
ttactctgtt tacagcaaaa ggctacctca tagttgatac atagcacacc tgtatgtatg    3646
ctgttccagc cttacaggtg gctgataatt ctctggtaca gaaccttttt atctgtatta    3706
taaatagcaa ttcacaactg catgtttctg acaaacactt gtgaataatg aagcatctcg    3766
ttttagttag caaagtctcc aaacatttcc ttaaaataat catgtattta gtttaaagaa    3826
ttatgggcac tgttcaactt aagcaaaaca gaacacggaa gcagtcttag aagcaccact    3886
ttgcccagag gtggaggttg aaggggtag cagggagagg ggttggtgta tgcaggtatt    3946
catgctaggc aaagagttta aaagacgcca atgtccttca tttactgtct gtgctgccct    4006
gaagccaagc gtattgcagc attatagccc caggcacata actaactagc actggcttgc    4066
caaggaatga acatgcaatg ccattactag ctattgaggg aaaagggtct gtgtgaagca    4126
tcactttgca gggattacta atggtggggc agcaggtctg tgaattaagt tatctcttga    4186
cctcaccctc atgtcaacac aaatgtaatt cctaaacaag atgcattgcc agtctcttag    4246
ccctgtaagc tgatcttttg ctacatggca gactataatg aaaacatttt tatacttggg    4306
tttctagtct tcactagaag gccttggatg tattttgca gttgaaagat ttagaaagat    4366
ttttacctgc ttataacttg gaagtttaga gtgcaatgta agaaaaaaga tcaagaaatg    4426
tcatgttatt agcatcagtc cacctccaat attgccgata ctttttttat tctggctcag    4486
ttttattttg caccagtgcg gccccaagtt actgctggtt gtatttagtt tgtgaatagg    4546
agcccataag tgttaataga cttttgtaaca ttcactataa gatgaattat acaggacatg    4606
ggaaatctca ttaagtctta aagttaattt aaattaattt atctgttttc tctaagaaat    4666
gtttatcata aaatatatat gtgtatttcc cctttggtta taaaatttgg gaaagtatgt    4726
acaagtgcag ctgcactgac tttaatttc tagatgtctt aatgagattt atttgtttta    4786
gagaagaaca tcttgttaaa agcatcaaac tctgtcttac atagctgtca acagcctctt    4846
taagatgtgg tggttgtatg atctgtgtct taattgttca gttagagtga aagttgacc    4906
tatgattcat ttttaaattt tatatttgga acaaagctgc aagttatggt aaagtactgt    4966
actgtgagaa gtattatgat atttaatgca tctgtggctt aacacttgtg agagttacca    5026
gcttgaaaat gatggtgttg actacctctt gaatcacatc tatcaaccac tggcacctac    5086
caccaagctg gcttcaatta gtatgtgttg cttttggta ttaacaacta accgtactag    5146
agaccaaagt gaaccctgat ttttatatgt ctttaataat ggtgttttat ctagtgtttt    5206
taaattatcc tgtgtagtat ttagattacc tcattgtcca ttttgactca tgttgtttac    5266
aagtgaaaat aaaacacttt gaactgtatg tttttaaaag acaaaaaagg ggtagatgtt    5326
tggaatgcgt ttcactcgca tgcagtcatc tggagggact gaagcactgt ttgcctttct    5386
gtacactctg ggttttatat tctcatttca tgcctaatgt cttattctgt caattatgga    5446
tatgttgagg tttaaaaaaa ttacttgatt aaaaataaaa catataacgt tggcattt      5504
```

<210> SEQ ID NO 2

```
<211> LENGTH: 250
<212> TYPE: PRT
<213> ORGANISM: Homo sapiens

<400> SEQUENCE: 2

Met Ala Glu Gly Gly Ala Ser Lys Gly Gly Glu Glu Pro Gly Lys
1               5                   10                  15

Leu Pro Glu Pro Ala Glu Glu Ser Gln Val Leu Arg Gly Thr Gly
                20                  25                  30

His Cys Lys Trp Phe Asn Val Arg Met Gly Phe Gly Phe Ile Ser Met
            35                  40                  45

Ile Asn Arg Glu Gly Ser Pro Leu Asp Ile Pro Val Asp Val Phe Val
50                      55                  60

His Gln Ser Lys Leu Phe Met Glu Gly Phe Arg Ser Leu Lys Glu Gly
65                  70                  75                  80

Glu Pro Val Glu Phe Thr Phe Lys Lys Ser Lys Gly Leu Glu Ser
                85                  90                  95

Ile Arg Val Thr Gly Pro Gly Gly Ser Pro Cys Leu Gly Ser Glu Arg
                100                 105                 110

Arg Pro Lys Gly Lys Thr Leu Gln Lys Arg Lys Pro Lys Gly Asp Arg
                115                 120                 125

Cys Tyr Asn Cys Gly Gly Leu Asp His His Ala Lys Glu Cys Ser Leu
130                     135                 140

Pro Pro Gln Pro Lys Lys Cys His Tyr Cys Gln Ser Ile Met His Met
145                 150                 155                 160

Val Ala Asn Cys Pro His Lys Asn Val Ala Gln Pro Ala Ser Ser
                165                 170                 175

Gln Gly Arg Gln Glu Ala Glu Ser Gln Pro Cys Thr Ser Thr Leu Pro
                180                 185                 190

Arg Glu Val Gly Gly His Gly Cys Thr Ser Pro Pro Phe Pro Gln
                195                 200                 205

Glu Ala Arg Ala Glu Ile Ser Glu Arg Ser Gly Arg Ser Pro Gln Glu
                210                 215                 220

Ala Ser Ser Thr Lys Ser Ser Ile Ala Pro Glu Glu Gln Ser Lys Lys
225                 230                 235                 240

Gly Pro Ser Val Gln Lys Arg Lys Lys Thr
                245                 250

<210> SEQ ID NO 3
<211> LENGTH: 34
<212> TYPE: DNA
<213> ORGANISM: Bacteriophage P1

<400> SEQUENCE: 3
ataacttcgt atagcataca ttatacgaag ttat                          34

<210> SEQ ID NO 4
<211> LENGTH: 34
<212> TYPE: DNA
<213> ORGANISM: Artificial Sequence
<220> FEATURE:
<223> OTHER INFORMATION: Synthetic mutant loxP (lox71) sequence

<400> SEQUENCE: 4
taccgttcgt atagcataca ttatacgaag ttat                          34

<210> SEQ ID NO 5
<211> LENGTH: 34
```

-continued

```
<212> TYPE: DNA
<213> ORGANISM: Artificial Sequence
<220> FEATURE:
<223> OTHER INFORMATION: Synthetic mutant loxP (lox66) sequence

<400> SEQUENCE: 5
ataacttcgt atagcataca ttatacgaac ggta                              34

<210> SEQ ID NO 6
<211> LENGTH: 81
<212> TYPE: DNA
<213> ORGANISM: Foot-and-mouth disease virus

<400> SEQUENCE: 6
aaaattgtcg ctcctgtcaa acaaactctt aactttgatt tactcaaact ggctggggat     60
gtagaaagca atccaggtcc a                                                81
```